(12) United States Patent
Janusson et al.

(10) Patent No.: US 7,780,741 B2
(45) Date of Patent: *Aug. 24, 2010

(54) SOCKET LINER INCORPORATING SENSORS TO MONITOR AMPUTEE PROGRESS

(75) Inventors: Hilmar Br. Janusson, Seltjarnarnes (IS); Freygardur Thorsteinsson, Reykjavik (IS); Gudjon G. Karason, Sollentuna (SE)

(73) Assignee: Össur hf, Reykjavik (IS)

( * ) Notice: Subject to any disclaimer, the term of this patent is extended or adjusted under 35 U.S.C. 154(b) by 1299 days.

This patent is subject to a terminal disclaimer.

(21) Appl. No.: 11/036,619

(22) Filed: Jan. 14, 2005

(65) Prior Publication Data

US 2005/0125078 A1    Jun. 9, 2005

Related U.S. Application Data

(63) Continuation of application No. 10/615,336, filed on Jul. 8, 2003, now Pat. No. 7,377,944.

(60) Provisional application No. 60/394,804, filed on Jul. 8, 2002.

(51) Int. Cl.
*A61F 2/80* (2006.01)

(52) U.S. Cl. ........................................ 623/36

(58) Field of Classification Search ............ 623/27–36, 623/56; 602/62, 63
See application file for complete search history.

(56) References Cited

U.S. PATENT DOCUMENTS

| | | | | |
|---|---|---|---|---|
| 3,548,420 A | * | 12/1970 | Spence | 623/37 |
| 3,751,733 A | * | 8/1973 | Fletcher et al. | 623/24 |
| 3,820,168 A | * | 6/1974 | Horvath | 623/24 |
| 3,949,388 A | | 4/1976 | Fuller | |
| 4,246,661 A | * | 1/1981 | Pinson | 623/25 |
| 4,321,057 A | | 3/1982 | Buckles | |
| 4,494,950 A | | 1/1985 | Fischell | |
| 4,655,779 A | * | 4/1987 | Janowiak | 623/37 |
| 4,685,925 A | * | 8/1987 | Childress et al. | 623/25 |
| 4,808,187 A | * | 2/1989 | Patterson et al. | 623/25 |

(Continued)

FOREIGN PATENT DOCUMENTS

| | | |
|---|---|---|
| EP | 0 870 485 A2 | 10/1988 |
| JP | 2001-218778 | 8/2001 |
| WO | WO 98/04182 | 5/1998 |
| WO | WO 00/74811 A2 | 12/2000 |

OTHER PUBLICATIONS

The International Search Report PCT/US03/22330.

(Continued)

*Primary Examiner*—Alvin J Stewart
(74) *Attorney, Agent, or Firm*—Knobbe Martens Olson & Bear LLP

(57) ABSTRACT

Disclosed is a device and method to aid in the monitoring of the health of an amputee's limb. The device employs a socket preferably including a liner. The liner may be constructed of an inner layer and an outer layer. The inner layer is configured to hold a plurality of sensors able to monitor the physiological health of the enclosed limb. The inner layer further employs a transmission device able to receive data from the sensors and send such data to an end user; the end user being a computer, the amputee, or a doctor. Through receipt of such data, the end user is aided in monitoring the health of the limb.

36 Claims, 6 Drawing Sheets

U.S. PATENT DOCUMENTS

| | | | |
|---|---|---|---|
| 4,831,531 A * | 5/1989 | Adams et al. ................... 701/2 |
| 4,895,574 A | 1/1990 | Rosenberg |
| 4,923,475 A * | 5/1990 | Gosthnian et al. ............. 623/37 |
| 5,054,488 A | 10/1991 | Muz |
| 5,108,456 A * | 4/1992 | Coonan, III ................... 623/37 |
| 5,133,776 A * | 7/1992 | Crowder ....................... 623/37 |
| 5,222,506 A | 6/1993 | Patrick et al. |
| 5,246,463 A * | 9/1993 | Giampapa .................... 623/24 |
| 5,247,938 A | 9/1993 | Silverstein et al. |
| 5,247,945 A | 9/1993 | Heinze et al. |
| 5,253,656 A | 10/1993 | Rincoe et al. |
| 5,258,037 A * | 11/1993 | Caspers ........................ 623/36 |
| 5,314,495 A * | 5/1994 | Kovacs ......................... 623/25 |
| 5,323,650 A | 6/1994 | Fullen et al. |
| 5,336,269 A * | 8/1994 | Smits ........................... 623/25 |
| 5,405,405 A * | 4/1995 | Love ............................ 623/37 |
| 5,408,873 A * | 4/1995 | Schmidt et al. ......... 73/862.625 |
| 5,413,611 A * | 5/1995 | Haslam et al. ................. 623/25 |
| 5,432,703 A * | 7/1995 | Clynch et al. ................ 700/163 |
| 5,443,525 A * | 8/1995 | Laghi ........................... 623/25 |
| 5,443,528 A | 8/1995 | Allen |
| 5,449,002 A | 9/1995 | Goldman |
| 5,464,443 A * | 11/1995 | Wilson et al. ................. 623/37 |
| 5,468,236 A | 11/1995 | Everhart et al. |
| 5,569,883 A | 10/1996 | Walter et al. |
| 5,571,208 A * | 11/1996 | Caspers ........................ 623/32 |
| 5,619,186 A | 4/1997 | Schmidt et al. |
| 5,728,167 A | 3/1998 | Lohmann |
| 5,830,136 A * | 11/1998 | Delonzor et al. ............. 600/323 |
| 5,840,047 A | 11/1998 | Stedham |
| 5,842,982 A | 12/1998 | Mannheimer |
| 5,888,213 A * | 3/1999 | Sears et al. ................... 623/24 |
| 5,888,230 A * | 3/1999 | Helmy .......................... 623/34 |
| 5,904,722 A * | 5/1999 | Caspers ........................ 623/34 |
| 5,944,661 A | 8/1999 | Swette et al. |
| 5,971,729 A | 10/1999 | Kristinsson et al. |
| 5,993,400 A * | 11/1999 | Rincoe et al. ............... 600/595 |
| 6,030,418 A | 2/2000 | Biedermann |
| 6,109,852 A * | 8/2000 | Shahinpoor et al. ............. 414/1 |
| 6,125,291 A | 9/2000 | Miesel et al. |
| 6,155,120 A * | 12/2000 | Taylor .................... 73/862.046 |
| 6,231,616 B1 * | 5/2001 | Helmy .......................... 623/34 |
| 6,244,873 B1 * | 6/2001 | Hill et al. .................... 434/236 |
| 6,287,253 B1 | 9/2001 | Ortega et al. |
| 6,344,062 B1 * | 2/2002 | Abboudi et al. ............... 623/24 |
| 6,379,393 B1 * | 4/2002 | Mavroidis et al. ............. 623/25 |
| 6,500,210 B1 * | 12/2002 | Sabolich et al. ............... 623/24 |
| 6,554,868 B1 * | 4/2003 | Caspers ........................ 623/34 |
| 6,560,471 B1 | 5/2003 | Heller et al. |
| 6,585,774 B2 * | 7/2003 | Dean et al. .................... 623/37 |
| 6,610,101 B2 * | 8/2003 | Herr et al. ..................... 623/24 |
| 6,618,934 B1 | 9/2003 | Feldman et al. |
| 6,660,042 B1 * | 12/2003 | Curcie et al. .................. 623/24 |
| 6,671,531 B2 | 12/2003 | Al-Ali et al. |
| 6,679,920 B2 | 1/2004 | Biedermann et al. |
| 6,740,123 B2 * | 5/2004 | Davalli et al. ................. 623/24 |
| 6,761,742 B2 * | 7/2004 | Caspers ........................ 623/34 |
| 6,846,331 B2 * | 1/2005 | Senoir ........................... 623/57 |
| 6,891,317 B2 * | 5/2005 | Pei et al. ..................... 310/328 |
| 6,922,592 B2 * | 7/2005 | Thompson et al. ............ 607/59 |
| 6,952,687 B2 * | 10/2005 | Andersen et al. .............. 706/12 |
| 6,969,941 B1 * | 11/2005 | Kapps et al. ............ 310/316.01 |
| 7,029,500 B2 * | 4/2006 | Martin ......................... 623/50 |
| 7,049,732 B2 * | 5/2006 | Pei et al. ..................... 310/365 |
| 7,147,667 B2 * | 12/2006 | Bedard ......................... 623/24 |
| 7,150,762 B2 * | 12/2006 | Caspers ........................ 623/33 |
| 7,377,944 B2 * | 5/2008 | Janusson et al. .............. 623/36 |
| 7,396,337 B2 * | 7/2008 | McBean et al. ................. 601/5 |
| 7,520,864 B2 * | 4/2009 | Yeh et al. ..................... 600/587 |
| 2002/0052663 A1 | 5/2002 | Herr et al. |
| 2002/0099450 A1 | 7/2002 | Dean, Jr. et al. |
| 2002/0123673 A1 | 9/2002 | Webb et al. |
| 2002/0156654 A1 | 10/2002 | Roe et al. |
| 2002/0183646 A1 | 12/2002 | Stivoric et al. |
| 2003/0040663 A1 | 2/2003 | Rule et al. |
| 2003/0078674 A1 * | 4/2003 | Phillips ........................ 623/37 |
| 2004/0010207 A1 * | 1/2004 | Flaherty et al. ............. 600/573 |
| 2004/0019288 A1 * | 1/2004 | Kinast ......................... 600/509 |
| 2004/0167638 A1 | 8/2004 | Caspers |
| 2006/0047215 A1 | 3/2006 | Newman et al. |

OTHER PUBLICATIONS

Robert M. Havey, et al. "Research Forum—Methodology—Measurements, Part II: Instrumentation and Apparatus", JPO 1996; vol. 8, Num 2, p. 50.
Office action in U.S. Appl. No. 10/615,336, mailed Jun. 29, 2004.
Office action in U.S. Appl. No. 10/615,336, mailed Dec. 8, 2004.
Office action in U.S. Appl. No. 10/615,336, mailed Feb. 16, 2005.
Office action in U.S. Appl. No. 10/615,336, mailed Aug. 10, 2005.
Office action in U.S. Appl. No. 10/615,336, mailed Dec. 14, 2005.
Office action in U.S. Appl. No. 10/615,336, mailed Apr. 5, 2006.
Office action in U.S. Appl. No. 10/615,336, mailed Sep. 20, 2006.
Claims as Allowed in U.S. Appl. No. 10/615,336, filed Nov. 6, 2007.

* cited by examiner

SOCKET LINER INCORPORATING SENSORS TO MONITOR AMPUTEE PROGRESS

PRIORITY APPLICATION

This is a continuation of U.S. patent application Ser. No. 10/615,336 (filed 8 Jul. 2003) now U.S. Pat. No. 7,377,944, which claims the benefit of U.S. Provisional Patent Application No. 60/394,804 (filed 8 Jul. 2002). Both of these priority applications are hereby incorporated by reference herein.

FIELD OF THE INVENTION

The field relates generally to a device and method for monitoring of the health of a person's limbs. More specifically, some embodiments relate to the analysis of data affecting the health of an amputee's limb. Some embodiments are targeted towards monitoring a limb through the use of a socket liner.

BACKGROUND OF THE INVENTION

Through the use of ever improving technology, amputees are finding more ways to function through the use of prosthetic devices. Often an amputee uses a socket placed over a limb which is thereby attached to the prosthetic device. The prosthesis may function as a leg, arm, foot, or hand for the amputee.

Use of sockets, however, may cause irritation, volumetric shrinkage and other adverse reactions to the user. Often liners, socks, sleeves, and other limb coverings are used to aid in the prevention of injury to the limb while the socket is in place. Damage to the limb may still occur despite the protection that a liner may provide.

There exists a need for new devices and methods that provide additional functionality to an amputee who uses a socket.

SUMMARY OF THE INVENTION

Briefly stated, embodiments of the present invention provide a device and method that allows an amputee or a person such as a doctor or prosthetist to monitor various characteristics of a limb. More specifically, the monitoring occurs when the limb is covered by a garment such as a socket or other item having a receiving portion adapted to receive the limb. Preferably, the limb is covered with a socket liner. Optionally the liner may be of a single or multiple layer construction. The liner is configured to hold sensors such as physiological sensors adapted to receive data from the limb throughout the day. The sensors may be constructed to receive a variety of physiological traits from the limb. Preferably, the liner further comprises a transmitter configured to receive data from the sensors and transmit such data to a computer, a user, a doctor or a prosthetist. The receiver of the data is thereby aided in monitoring the health of the enclosed limb.

Accordingly, in one embodiment, a socket is provided for receiving a limb of an amputee. The socket comprises a liner adapted to receive a limb of an amputee, and one or more sensors provided in the liner, the sensors being adapted to monitor physiological data received therein. In one embodiment the liner includes a plurality of grooves for receiving the sensors. The sensors in one embodiment are strips provided along a surface of the liner. In other embodiments, the sensors may be composed of various shapes and sizes. For example, ring-like sensors could be placed around or within the liner. Also, smaller sensors could be placed at discreet locations along the length of the liner. These smaller sensors may be composed of circular or other geometric shapes. In one embodiment the liner is made from two parts adhered together.

One embodiment of a socket liner includes a liner and one or more sensors provided in the liner adapted to monitor data. One liner includes an inner layer, an outer layer, and a sensor in a channel used to monitor physiological characteristics of a limb. Another liner holds a physiological sensor for receiving data from a limb and transmitter for sending the data to a receiver. Another embodiment discloses a garment with a receiving portion to hold a plurality of sensors wherein the garment is configured to transmit received data to an end user. Also provided is a method of monitoring the physiological characteristics of a limb by using data accumulated from a liner having one physiological sensor located therein.

DETAILED DESCRIPTION OF THE PREFERRED EMBODIMENTS

Figure 1:
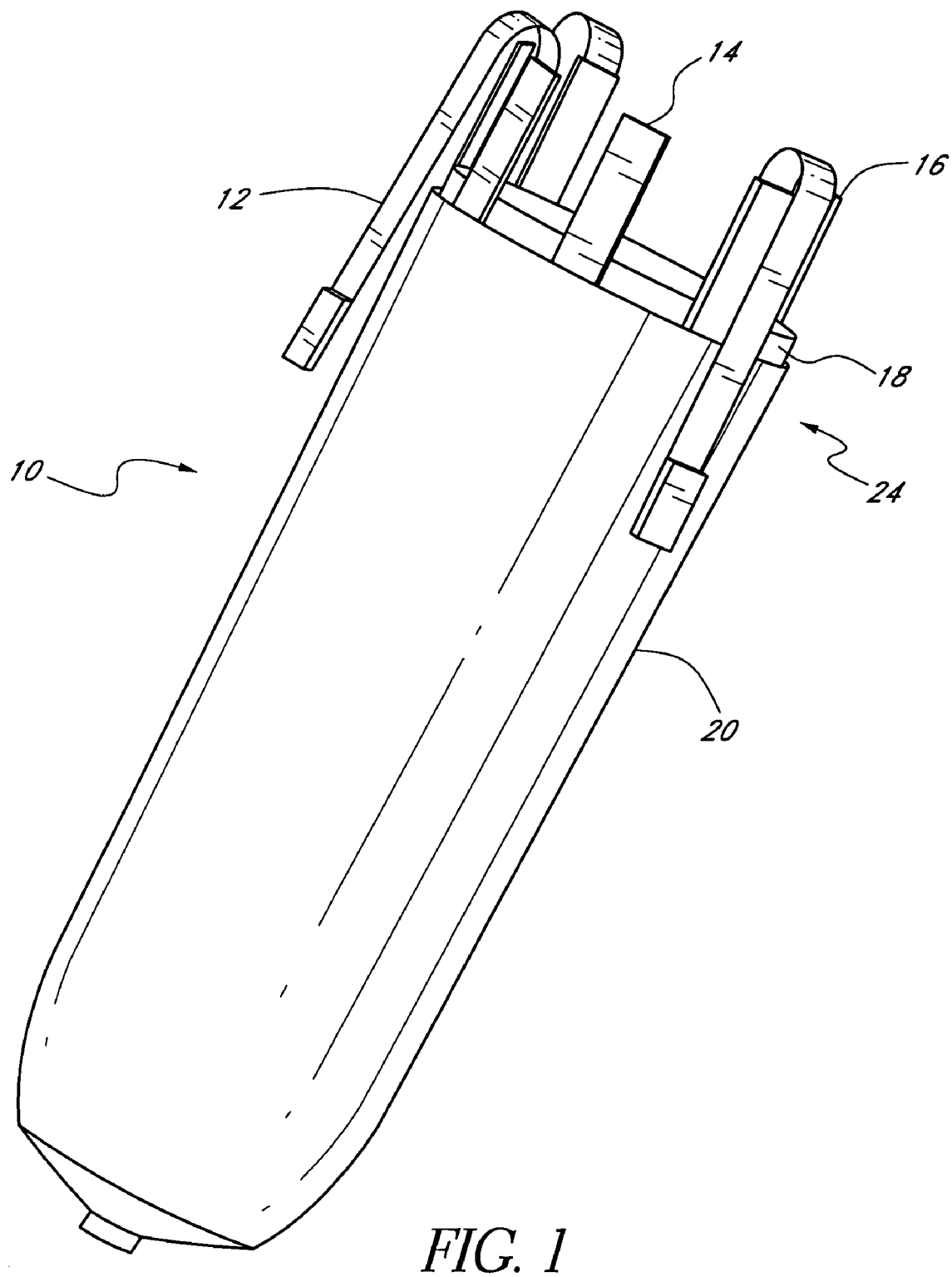
FIG. 1 depicts an assembled embodiment of a two-layered socket liner.

Preferred embodiments of the present invention are directed to developing an interface for amputees, where physical data for a limb can be gathered over a period of time in normal action. In one embodiment a socket is used as an interface between the limb and a prosthesis. Amputees may use liners to provide suspension and comfort inside of the socket. A liner may be made of silicone or other material and may provide a locking mechanism with the socket. Locking liners incorporate a pin and are relied upon for suspension of the socket. Non-locking liners or cushion liners are generally used for comfort purposes and use belts or other mechanisms to provide suspension of the socket. The term liner is meant to be construed as a broad term and may encompass a sock, a sleeve, an insert or other coverings placed over an amputee's limb. At the same time, liner is meant to be used in its plain and ordinary meaning. In one embodiment, described further below, sensors are incorporated into the socket liner that is placed between the limb and the socket. In alternative embodiments, sensors may be incorporated into a socket sock or in the socket itself. Typically socks provide cushioning for the limb and add volume to the limb that is lost throughout the day.

Preferably, sensors are placed in a silicone or other polymer material (e.g., thermoplastic elastomers or polyurethane) that comprise the socket liner. Sensors may include, but are not limited to:

Oxygen sensors for the measurement and mapping of peripheral oxygen, such as by means of an array of high sensitivity Spo2 sensors;

Pressure sensors detecting the fit of the liner and/or socket over the limb;

Temperature sensors;

Sensors to measure blood pressure;

Humidity sensors;

Sensors to measure glucose;

Sensors to measure limb movement within the liner and/or socket throughout the gait;

Sensors to measure volume fluctuation of the limb throughout the day;

Sensors to measure body fat;

Activity monitoring sensors, i.e. how long the prosthesis is worn from day to day and whether there are high periods of activity.

Sensors to measure the shear forces exerted on a limb by the liner and/or socket.

It will be appreciated that other sensors may be used in the liner for different applications and for other diagnostic or physiological measurements.

Data obtained by the sensors can be sent to a remote location to a rehabilitation doctor and/or a CPO (Certified Prosthetist/Orthotist) using telecommunications equipment incorporated into or with the liner. This approach assists amputees to integrate into the society and maximize the comfort and use of their prosthesis. Another objective is to gather medical information about amputees in a statistical way, thus giving possibilities for better treatment. The sensors may be held in place within the liner through the use of grooves, channels, or pockets. The pockets may have opened or closed ends. Alternatively, a combination of grooves, channels, and pockets may exist. Further, the sensors may extend over the liner. The sensors may be made of rigid, soft, or a combination of rigid and soft materials.

Two ways that sensors can be incorporated into a socket liner are integrated sensors, and sensors placed in-between layers of the socket liner. Sensors, however may be placed into socks, socket inserts, the socket itself, as well as other layers of material that may be incorporated into a device placed over an amputee's limb.

FIG. 1 illustrates one embodiment of a socket liner incorporating physiological sensors, more preferably pressure sensors 14, 16 and oxygen sensors 12. The term "physiological sensor" is meant to define a broad term as well as its ordinary meaning. Physiological sensors may be used to measure peripheral oxygen, temperature, humidity, body fat, blood gasses, blood pressure, blood glucose levels, and other related data such as described above. Physiological pressure sensors 14, 16 may be used to monitor the pressure exerted by the limb onto the liner which can be used as a measure of a patient's health. The pressure sensors 14, 16 may also monitor the pressure exerted by the liner 10 and/or socket on the limb. Oxygen sensors 12 may be used to measure peripheral oxygen such as described above.

The liner 10 may comprise a single or multiple layers. Preferably the liner 10 is made in two layers 18, 20. In one embodiment, the inner layer 18 preferably includes up to six longitudinal grooves or channels 22 that the sensors 12, 14, 16 are placed in. Sensors 12, 14, 16 may be placed in one or more of the grooves 22. Once the sensors 12, 14, 16 have been correctly positioned, the outer layer 20 is positioned over the inner layer 18. Next, the inner 18 and outer layers 20 are adhered together. Both parts are preferably made of silicone, although other suitable materials may be used as well.

Figure 2:
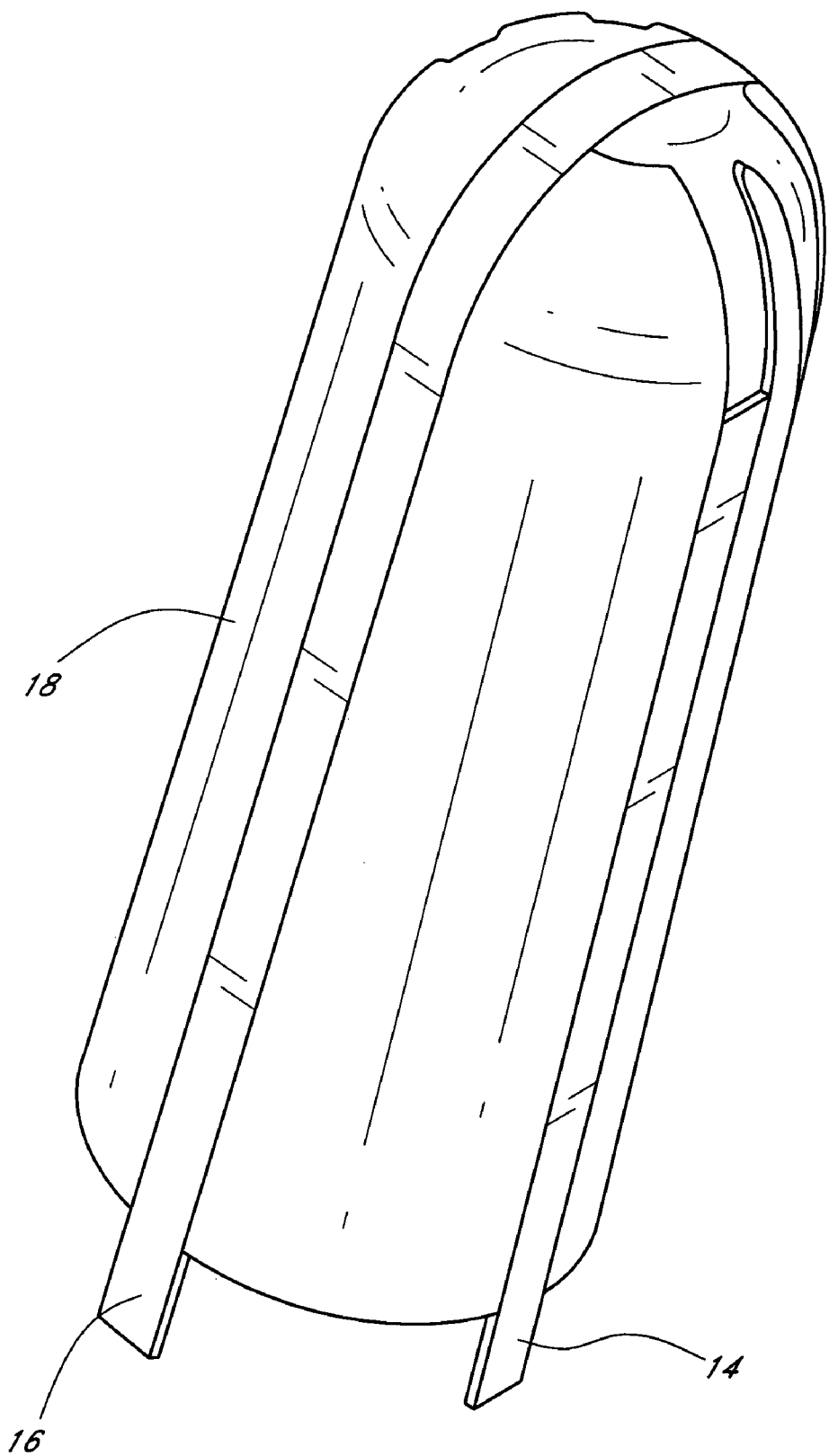
FIG. 2 shows an inner liner with a pressure sensor wrapping over its bottom layer.
Figure 3:
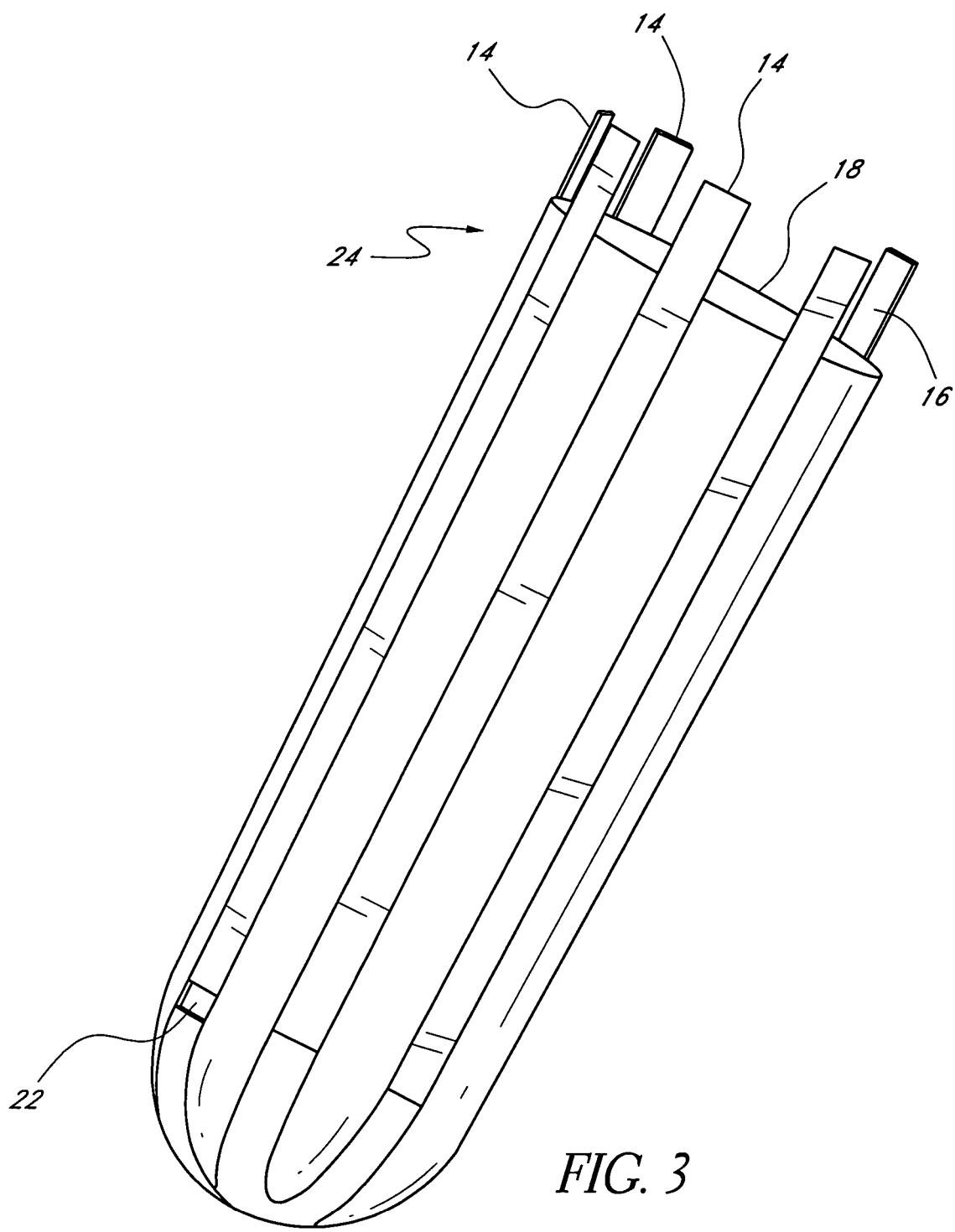
FIG. 3 depicts an alternative view of the inner liner of FIG. 2.

FIGS. 2 and 3 illustrate the inner layer 18 of the liner 10 with six pressure sensors 14, 16 provided therein. As shown in greater detail in FIGS. 6-9, in one embodiment there are provided five short pressure sensors 14, and one long pressure sensor 16. The five short pressure sensors 14 are preferably provided about 45° apart along the circumference of the liner 10, with the one long pressure sensor 16 being positioned 180° opposite the centralmost of the five short sensors 14. In an example where a 300 mm long silicone liner 10 is used, the short sensors 14 are preferably about 260 mm long, and the one long sensor 16 is about 410 mm long, wrapping around the bottom of the inner layer 18 to the opposite side. These lengths provided above refer to the total length of the flexible part of the respective sensor 14, 16. The sensors 14, 16 preferably further include a rigid part 26, located above the upper edge 24 of the liner 10 (as shown in FIGS. 6-9). Any portion of the sensors may be constructed of soft or rigid materials. The sensors may be constructed of silicone and other similar polymer materials. In one embodiment the sensors may be made of a metal and foam combination. In the illustrated embodiment, the rigid part 26 is preferably about 30 mm long.

Figure 4:
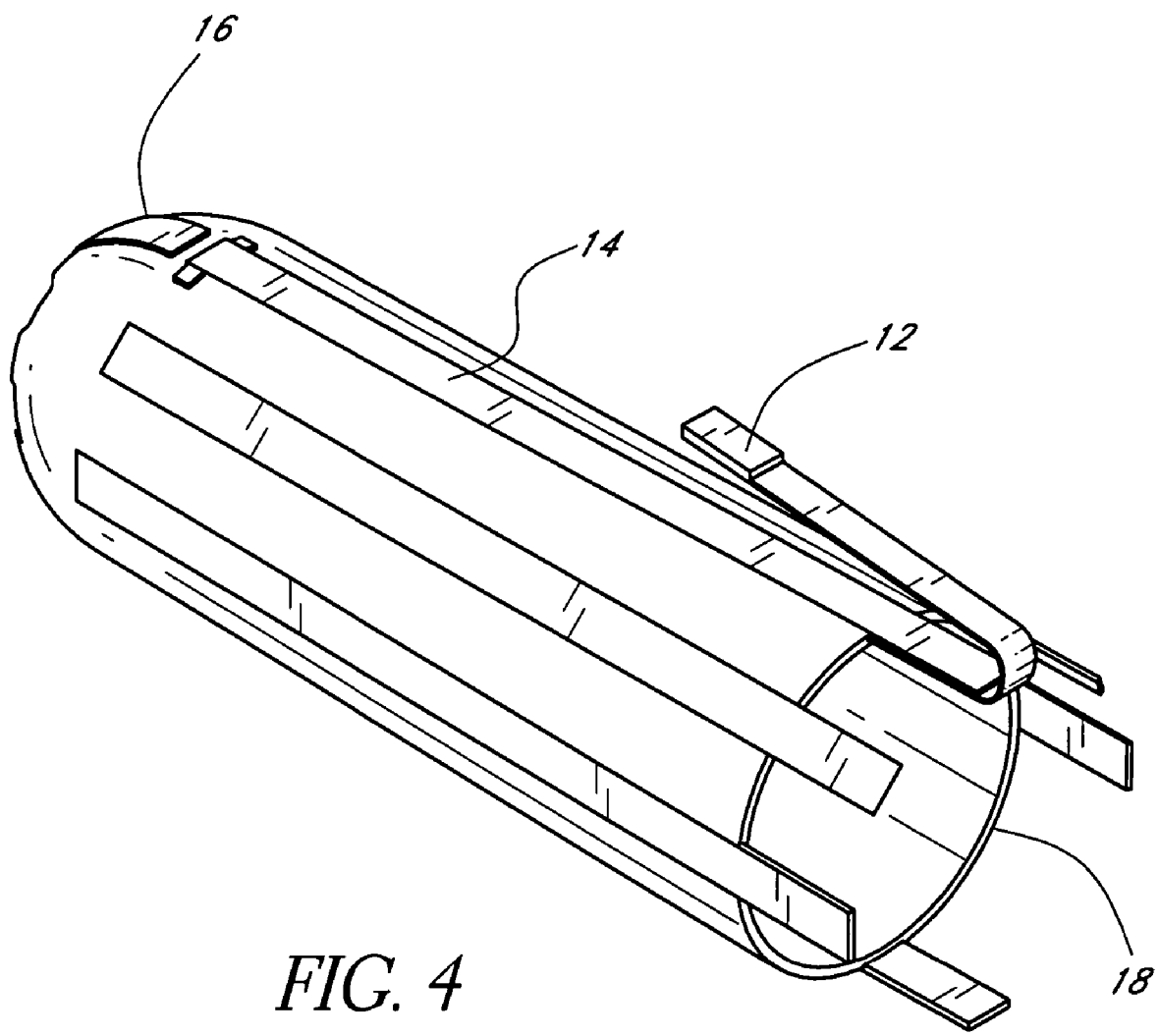
FIG. 4 shows an embodiment of an inner layer of a socket liner having an oxygen sensor and pressure sensors.
Figure 5:
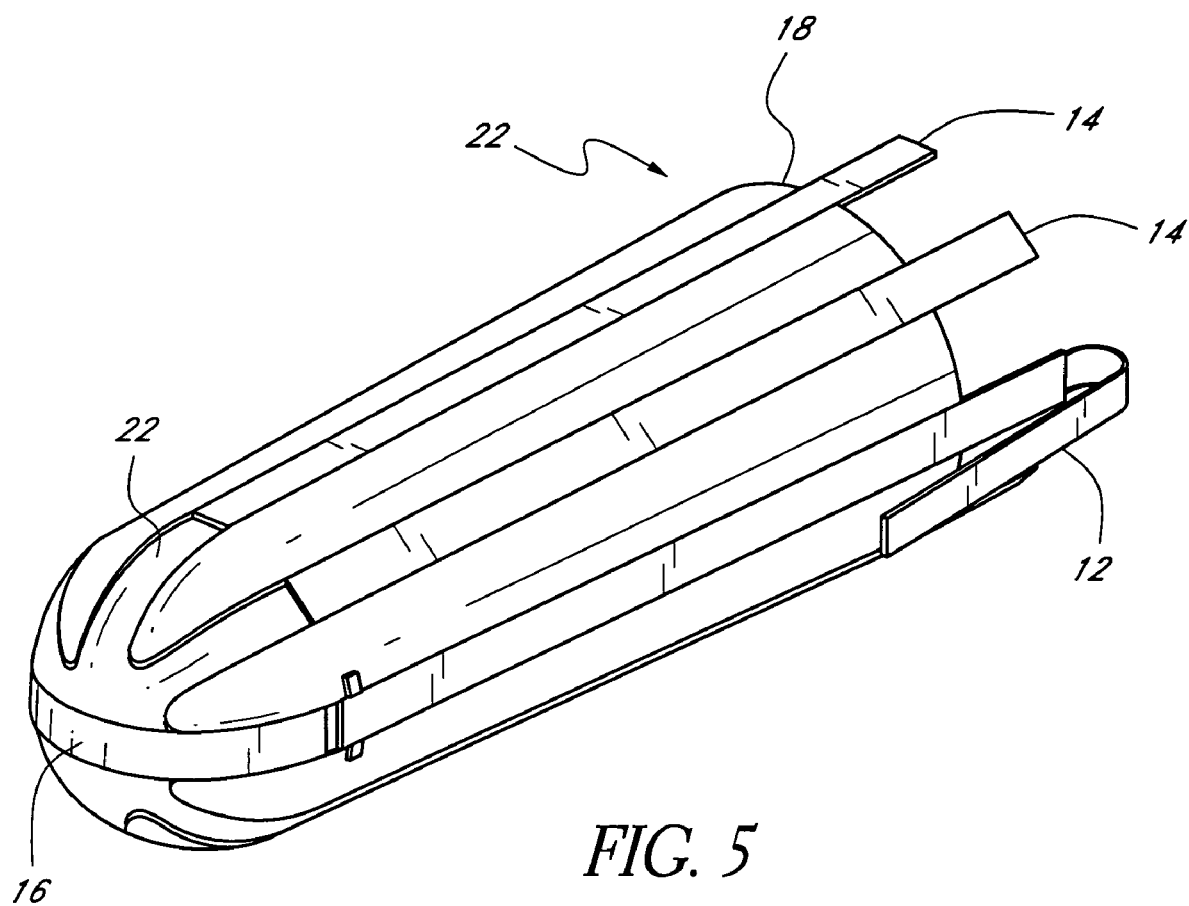
FIG. 5 depicts an alternative view of the socket liner of FIG. 4.
Figure 6A:
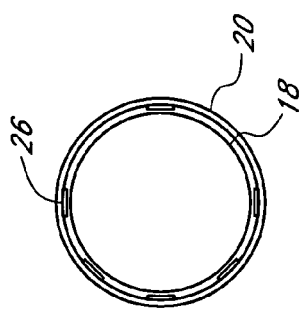
FIG. 6a is a top end view of the liner of FIG. 6.
Figure 9:
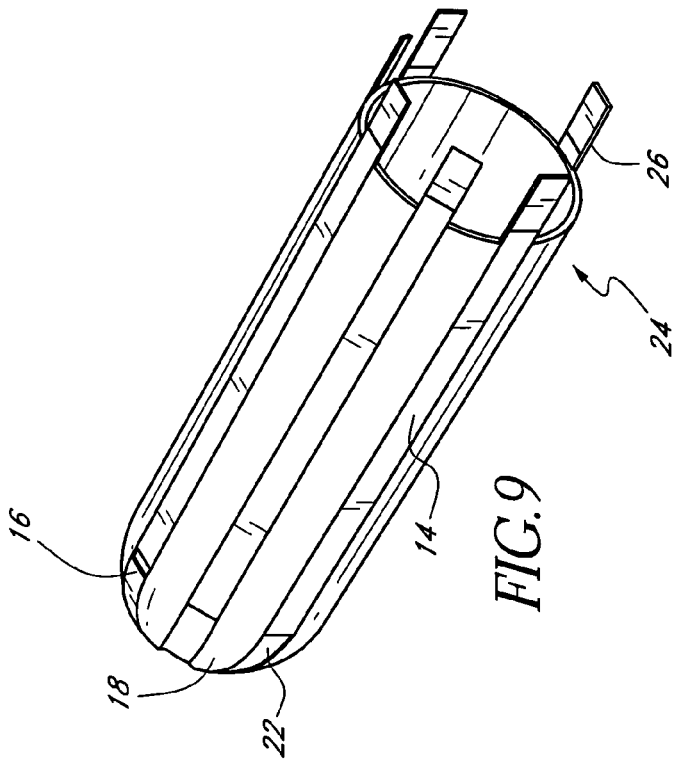
FIG. 9 is an isometric view of an inner layer with pressure sensors.
Figure 6:
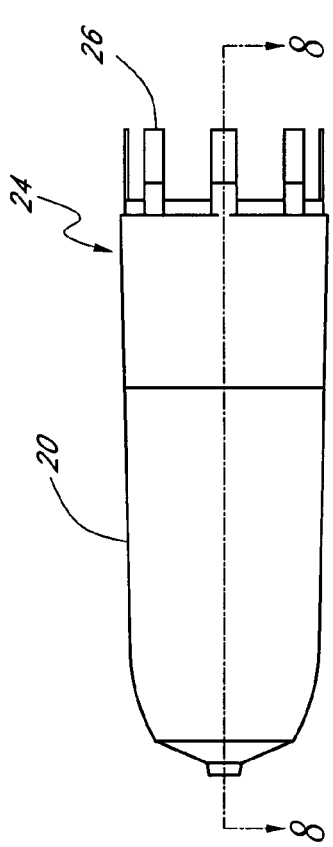
FIG. 6 is a side view of a two-layered liner.
Figure 7:
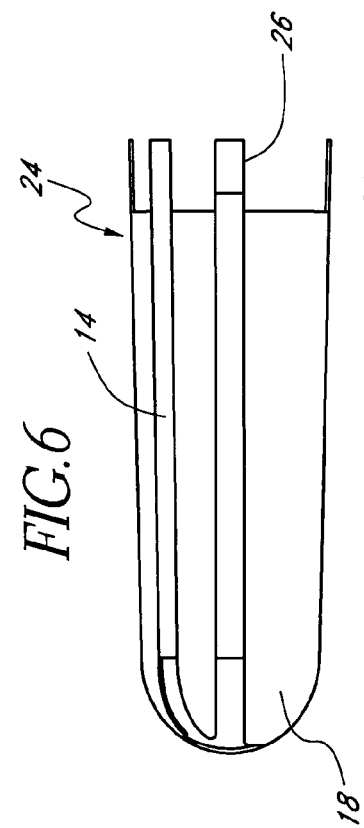
FIG. 7 is a side view of an inner layer with sensors.
Figure 8:
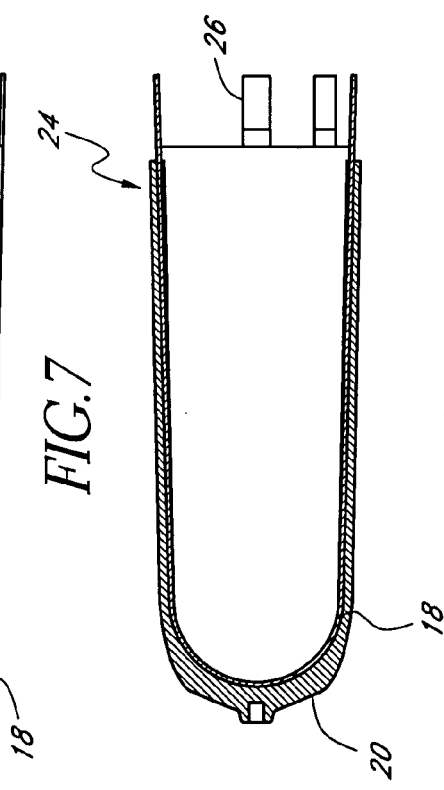
FIG. 8 is a cross-sectional view of a two-layered liner.

FIGS. 4 and 5 illustrate the inner layer 18 of the liner provided with an oxygen sensor 12 therein. The oxygen sensor 12 may be positioned in a variety of positions including next to, under or extending over the pressure sensors 14, 16. As illustrated in FIGS. 4 and 5, an oxygen sensor 12 is provided over a pressure sensor 14, and both the oxygen sensor 12 and pressure sensors 14, 16 extend over the edge 24 of the liner 10. In another embodiment (not shown), the sensors 12, 14, 16 are completely positioned between the inner 18 and outer layers 20 of the liner 10. In another embodiment, the oxygen sensors 12 are incorporated into the liner 10 without being connected to a pressure sensor 14, 16. Alternatively, oxygen sensors 12 may be incorporated into a liner 10, sock, insert, and/or socket in combination with any of the previously mentioned physiological sensors 12, 14, 16 or by themselves. As illustrated in FIG. 1, in one embodiment of an assembled liner 10, three oxygen sensors 12 are provided in the liner 10.

It will be appreciated that the number and arrangement of sensors 12, 14, 16 in the liner 10 can be varied. It will also be appreciated that other ways of incorporating the sensors 12, 14, 16 into the liner 10 can be used as well. Furthermore, sensors 12, 14, 16 need not be positioned in the liner 10 and may be positioned in the socket itself. Other variations of the described device are also contemplated. Thus, the scope of this invention is not to be limited to the preferred embodiments described above.

We claim:

1. A socket liner system for receiving a limb of an amputee, the system comprising:
    a liner adapted to receive a residual limb of an amputee, the liner comprising a tubular body having a longitudinal axis that extends from a closed distal end of the liner to an open proximal end of the liner, wherein the liner is generally symmetrical about the longitudinal axis; and
    a sensor provided in the liner that extends from one side of the liner tubular body to another side of the liner tubular body and passes over the closed distal end of the liner, the sensor configured to gather physiological data received therein over at least a portion of a day for subsequent monitoring of patient health.

2. The socket liner system of claim 1, further comprising a data gathering device configured to store the physiological data gathered by the sensor.

3. The socket liner system of claim 2, wherein the data gathering device is a computer.

4. The socket liner system of claim 1, wherein the sensor is a pressure sensor.

5. The socket liner system of claim 1, wherein the liner includes a groove for receiving the sensor.

6. The socket liner system of claim 1, wherein the sensor is a strip provided along an inner surface of the liner.

7. The socket liner system of claim 1, wherein the liner is adapted to receive a residual portion of an amputated leg.

8. A socket liner system for receiving a residual limb of an amputee, the system comprising:
- a liner adapted to receive a residual limb of an amputee, the liner comprising a tubular body that extends generally symmetrically along a longitudinal axis from a closed distal end of the liner to an open proximal end of the liner, the liner including an inner layer having a pocket and an outer layer that provides an interface between the inner layer and a socket;
- a sensor having a flexible portion and a rigid portion provided in the pocket of the liner inner layer, the sensor being configured to gather physiological data received therein over a desired length of time for subsequent monitoring of patient health; and
- a memory configured to store the physiological data gathered by the sensor.

9. The socket liner system of claim 8, wherein the sensor is a strip provided in the liner inner layer.

10. The socket liner system of claim 8, further comprising a transmitter configured to transmit the physiological data to an end user to monitor the health of the residual limb.

11. The socket liner system of claim 8, wherein the sensor extends from one side of the liner tubular body to another side of the liner tubular body and passes over the closed distal end of the liner.

12. A socket liner system for receiving a limb of an amputee, the system comprising:
- a liner adapted to receive a residual limb of an amputee, the liner comprising a tubular body that extends generally symmetrically along a longitudinal axis from a closed distal end of the liner to an open proximal end of the liner;
- a sensor provided in the liner that extends from one side of the liner tubular body to another side of the liner tubular body and passes over the closed distal end of the liner, the sensor being configured to gather data regarding physiological characteristics of the limb over a desired length of time, wherein the sensor is in communication with a transmitter that is configured to send the gathered physiological characteristic data to a receiver to allow an end user to analyze the physiological characteristic data; and
- a computer storing the physiological characteristic data gathered by the sensor.

13. The socket liner system of claim 12, wherein the sensor is a pressure sensor.

14. The socket liner system of claim 12, wherein the liner includes a groove for receiving the sensor.

15. The socket liner system of claim 12, wherein the liner includes a pocket for receiving the sensor.

16. The socket liner system of claim 12, wherein the sensor is a pressure sensor comprising a strip provided along an inner surface of the liner.

17. The socket liner system of claim 12, wherein the liner is made from two parts adhered together.

18. The socket liner system of claim 12, wherein the liner is adapted to receive a portion of an amputated leg.

19. A socket liner for receiving a residual limb of an amputee, the socket liner comprising:
- an inner liner having an elongate sleeve with a cavity configured to receive a residual limb of an amputee, the inner liner having a tubular shape extending generally symmetrically about a longitudinal axis from a closed distal end of the inner liner to an open proximal end of the inner liner;
- an outer liner positioned over the inner liner and having an exterior surface configured to receive a socket thereover, the outer liner having a tubular shape extending generally symmetrically about a longitudinal axis from a closed distal end of the outer liner to an open proximal end of the outer liner; and
- a sensor configured to receive physiological data from the residual limb, the sensor positioned in a groove between the inner liner and the outer liner.

20. The socket liner of claim 19, wherein the sensor is an elongate strip configured to be wrapped around a portion of the inner liner.

21. The socket liner of claim 19, further comprising a plurality of sensors.

22. The socket liner of claim 19, further comprising an adhesive disposed between the inner liner and the outer liner.

23. The socket liner of claim 19, further comprising a transmitter configured to send data to a receiver to allow an end user to analyze physiological characteristics of the residual limb.

24. The socket liner of claim 19, wherein the sensor is selected from the group consisting of an oxygen sensor and a pressure sensor.

25. The socket liner of claim 19, wherein the sensor comprises an extending portion that extends outwardly from the open proximal end of the socket liner in a generally longitudinal direction.

26. A prosthetic system for a limb of an amputee, the system comprising:
- a prosthetic socket;
- a liner adapted to receive a residual limb of an amputee therein and to be removably positioned within the socket, the liner comprising a tubular body having a longitudinal axis that extends from a closed distal end of the liner to an open proximal end of the liner, the liner being generally symmetrical about the longitudinal axis;
- a sensor provided in the liner, the sensor embedded within the liner wherein the sensor is disposed between an innermost surface and an outermost surface of a liner wall, and the sensor configured to gather physiological data of the residual limb over at least a portion of a day for subsequent monitoring of patient health;
- a memory configured to store the physiological data gathered by the sensor; and
- a prosthetic device operatively coupled to the socket.

27. The prosthetic system of claim 26, wherein the prosthetic device is a foot.

28. The prosthetic system of claim 26, wherein the prosthetic device is a leg.

29. The prosthetic system of claim 26, wherein the sensor is a strip sensor.

30. The prosthetic system of claim 26, wherein the sensor passes over the closed distal end of the tubular body.

31. The prosthetic system of claim 26, wherein the sensor comprises a flexible portion and a rigid portion.

32. The prosthetic system of claim 26, wherein the sensor extends out from the open proximal end of the liner and is folded back onto itself such that at least two sensors overlap one another.

33. A socket liner system for receiving a residual limb of an amputee, the system comprising:
- a liner comprising a tubular body that extends generally symmetrically along a longitudinal axis from a closed distal end to an open proximal end, the liner comprising an inner layer and an outer layer, at least one of the inner and outer layers defining a channel; and
- a sensor disposed in the channel such that the inner and outer layers are positionable adjacent each other at locations about the sensor, the sensor configured to gather physiological data from a residual limb received in the liner over a desired length of time for subsequent monitoring of patient health, wherein the liner is adapted to be inserted in a prosthetic socket so that the outer layer provides an interface between the inner layer and the socket.

34. The socket liner system of claim 33, wherein the sensor is a strip sensor.

35. The socket liner system of claim 33, further comprising a transmitter adapted to transmit the physiological data to an end user to monitor the health of the residual limb.

36. The socket liner system of claim 33, further comprising a memory configured to store the physiological data gathered by the sensor.

* * * * *